United States Patent
Fleming et al.

(10) Patent No.: US 8,078,478 B2
(45) Date of Patent: *Dec. 13, 2011

(54) METHOD, APPARATUS, AND DATA PROCESSOR PROGRAM PRODUCT CAPABLE OF ENABLING MANAGEMENT OF ATHLETICISM DEVELOPMENT PROGRAM DATA

(75) Inventors: John C. Fleming, Round Rock, TX (US); Thomas D. Mixon, Austin, TX (US)

(73) Assignee: Nike, Inc., Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/566,444

(22) Filed: Sep. 24, 2009

(65) Prior Publication Data

US 2010/0017402 A1   Jan. 21, 2010

Related U.S. Application Data

(63) Continuation of application No. 09/965,338, filed on Sep. 27, 2001, now abandoned.

(51) Int. Cl.
  *G06Q 10/00* (2006.01)
  *H04Q 7/20* (2006.01)
  *A63B 21/00* (2006.01)
(52) U.S. Cl. .......... 705/1.1; 705/2; 428/8; 428/4; 428/1; 455/456.3; 600/300
(58) Field of Classification Search .................. None
  See application file for complete search history.

(56) References Cited

U.S. PATENT DOCUMENTS

| | | |
|---|---|---|
| 4,186,388 A | 1/1980 | Robinson |
| 4,645,458 A | 2/1987 | Williams |
| 5,031,903 A | 7/1991 | Clarke |
| 5,469,740 A | 11/1995 | French et al. |
| 5,496,204 A | 3/1996 | Brown et al. |
| 5,697,791 A | 12/1997 | Nashner et al. |
| 5,720,200 A | 2/1998 | Anderson et al. |
| 5,897,457 A | 4/1999 | Mackovjak |
| 6,002,336 A | 12/1999 | Widding et al. |
| 6,010,452 A * | 1/2000 | Harcourt ...................... 600/300 |
| 6,073,489 A | 6/2000 | French et al. |
| 6,086,379 A | 7/2000 | Pendergast et al. |
| 6,155,957 A | 12/2000 | Worley et al. |
| 6,181,647 B1 | 1/2001 | Tipton et al. |

(Continued)

OTHER PUBLICATIONS

Peter J. Maud and Carl Foster, Physiological Assessment of Human Fitness, 1995, pp. 1-7, 37-54, 115-132, 167-187, 221-225, Human Kinetics, USA.

(Continued)

*Primary Examiner* — Matthew Brooks
(74) *Attorney, Agent, or Firm* — Shook, Hardy & Bacon L.L.P.

(57) ABSTRACT

Various aspects of one or more methods, apparatuses and data processor program products capable of enabling management of data associated with an athleticism development program are disclosed herein. These various aspects include maintaining a database including subscriber performance data for a plurality of athleticism development program subscribers and facilitating preparation of a subscriber performance report for a specified one of the plurality of athleticism development program subscribers. The subscriber performance data is capable of enabling an attained standardized athleticism level to be determined for each one of the athleticism development program subscribers. The implementation of standardized athleticism levels is advantageous as it supports a measurable plan of progress for motivating a subscriber and trainer to meet their individual and mutual goals.

19 Claims, 12 Drawing Sheets

U.S. PATENT DOCUMENTS

| | | | |
|---|---|---|---|
| 6,186,961 | B1 | 2/2001 | Hanoun |
| 6,308,565 | B1 | 10/2001 | French et al. |
| 6,430,997 | B1 | 8/2002 | French et al. |
| 6,565,449 | B2 | 5/2003 | Buhler |
| 6,585,622 | B1 | 7/2003 | Shum et al. |
| 6,607,483 | B1 | 8/2003 | Holland |
| 6,649,905 | B2 | 11/2003 | Grenlund |
| 6,746,370 | B1 * | 6/2004 | Fleming et al. ............... 482/1 |
| 6,765,726 | B2 | 7/2004 | French et al. |
| 6,885,971 | B2 | 4/2005 | Vock et al. |
| 7,072,789 | B2 | 7/2006 | Vock et al. |
| 7,278,966 | B2 | 10/2007 | Hjelt et al. |
| 7,480,512 | B2 * | 1/2009 | Graham et al. ............ 455/456.3 |
| 2004/0225467 | A1 | 11/2004 | Vock et al. |
| 2004/0229729 | A1 | 11/2004 | Albert et al. |
| 2005/0014113 | A1 | 1/2005 | Fleck et al. |
| 2005/0069853 | A1 | 3/2005 | Tyson et al. |
| 2006/0084850 | A1 | 4/2006 | Spinner et al. |
| 2007/0213126 | A1 | 9/2007 | Deutsch et al. |
| 2007/0219059 | A1 * | 9/2007 | Schwartz et al. ............... 482/8 |
| 2007/0232455 | A1 * | 10/2007 | Hanoun ........................... 482/8 |
| 2007/0272011 | A1 | 11/2007 | Chapa, Jr. |
| 2008/0261776 | A1 * | 10/2008 | Skiba ............................... 482/8 |
| 2010/0017402 | A1 * | 1/2010 | Fleming et al. ............... 707/5 |

OTHER PUBLICATIONS

Dennis K. Flood, Practical Math for Health Fitness Professionals, 1996, pp. 1-4, Human Kinetics, USA.

John Hawley and Louise Burke, Peak Performance: Training and Nutritional Strategies for Sport, 1998, pp. 32-37, 50-76, 148-151, Allen & Unwin, Australia.

Vladimir M. Zatsiorsky, Science and Practice of Strength Training, 1995, pp. 200-221, Human Kinetics, USA.

Mel Cunningham Siff, Supertraining, 1996, pp. 86-88, 144-163, 176-192, 203-210, 254-260, 309-326, 384-396, 423-434, Supertraining Institute.

Australian Sports Commission, Physiological Tests for Elite Athletes, 2000, pp. 37-49, 224-237, Human Kinetics, USA.

American College of Sports Medicine, ACSM's Guidelines for Exercise Testing and Prescription, 1995, pp. 49-84, 110-148, Williams & Wilkins, USA.

Presidential Physical Fitness Award, http://www.indiana.edu/~preschal, Mar. 1, 2000, retrieved on Oct. 23, 2008, retrieved from the Internet Wayback Machine: http://web.archive.org/web/20000301151029/www.indiana.edu~preschal/testitems.html, and http://web.archive.org/web/20000301100939/www.indiana.edu/~preschal/qualifying/presidential.html.

Fitnessgram, http://www.cooperinst.org, Aug. 17, 2000, retrieved on Oct. 27, 2008, retrieved from internet wayback machine http://web.archive.org/web/20000817163237/http://www.cooperinst.org/5.html and http://web.archive.org/web/20000901054651/www.cooperinst.org/fgram.html.

Advanced Fitness Designs Inc., Fiteval 2000 User's Guide, Jun. 2000, Advanced Fitness Designs, Inc.

Fitnessgram http://www.americanfitness.net, Aug. 16, 2000, retrieved on Nov. 7, 2008, retrieved from the Internet Wayback Machine http://web.archive.org/web/20000816235846/www.americanfitness.net/fitnessgram.

International Search Report and Written Opinion in International Patent Application PCT/US05/40493, Filed Jul. 13, 2006.

M. Yessis; "The Athlete Defined: A Soviet System of Rank"; Strength & Conditioning Journal, 3:4, pp. 20-1, 1981.

D. Pfaff "Norm-based field testing"; New Studies in Athletics, 8:1, pp. 51-55, 1993.

S. Pilicz et al.; "Physical Fitness Score Tables of Polish Youth—Criteria for Measuring Aerobic Capacity By The Cooper Test"; Monograph; Warsaw; 2005.

R. Stupnicki et al.; "Standardisation of somatic and physical fitness variables"; Physical Education and Sport, 49, pp. 72-79; 2005.

T. Olds et al.; "Worldwide variation in the performance of children and adolescents: An analysis of 109 studies of the 20-m shuttle run test in 37 countries", Journal of Sports Sciences, 24 (10), pp. 1025-1038; Oct. 2006.

J.R. Mureika et al.; "The 1999 Mercier Scoring Tables: A How-To Guide"; Athletics: Canada's National Track and Field/Running Magazine; Apr./May 2000.

V. Trkal; "The Development of Combined Events Scoring Tables and Implications for the Training of Decathletes", New Studies in Athletics, 18:4, pp. 7-14; 2003.

K. Stauffer; "The Comparison of the Max Jones Quadrathlon with the Vertical Jump and Wingate Cycle Tests as a Method to Assess Anaerobic Power in Female Division I College Basketball Players"; Doctoral Dissertation; University of Pittsburg 2005.

W. Westera; "Decathlon: Towards a balanced and sustainable performance assessment method"; New Studies in Athletics, 21:1, pp. 39-51; 2006.

B. Grammaticos; "The physical basis of scoring the athletic performance"; New Studies in Athletics, 22:3 pp. 47-53; 2007.

Office Action mailed Feb. 16, 2011 in U.S. Appl. No. 11/269,161.
Office Action mailed May 29, 2008 in U.S. Appl. No. 09/965,338.
Office Action mailed Jul. 7, 2010 in U.S. Appl. No. 11/269,161.
Office Action mailed Dec. 14, 2009 in U.S. Appl. No. 11/269,161.
Office Action mailed Apr. 15, 2009 in U.S. Appl. No. 11/269,161.

* cited by examiner

602 —

| LEVEL | Resting Heart Rate | Body Fat | 3 Minute | Push-Up | Sit-Up | 1 ½ Mile Run | Flex | T-Test | 40 Yd. Sprint |
|---|---|---|---|---|---|---|---|---|---|
| L7 | 1111 | 1740 | 1076 | 993 | 1000 | 1014 | 1111 | 1015 | 975 |
| L6 | 983 | 1624 | 966 | 800 | 800 | 812 | 1000 | 892 | 893 |
| L5 | 923 | 1436 | 876 | 542 | 533 | 713 | 889 | 803 | 759 |
| L4 | 857 | 1304 | 801 | 284 | 266 | 649 | 833 | 715 | 630 |
| L3 | 811 | 1104 | 732 | 129 | 133 | 586 | 667 | 602 | 520 |
| L2 | 740 | 836 | 675 | 65 | 67 | 550 | 556 | 498 | 390 |
| Novice | 681 | 600 | 607 | 13 | 12 | 468 | 389 | 377 | 310 |

604 —

| LEVEL | White | Red | Black |
|---|---|---|---|
| L7 |  |  | 1076 |
| L6 |  | 1740 | 966 |
| L5 |  | 1075 | 690 |
| L4 | 1450 | 890 |  |
| L3 | 987 | 850 |  |

FIG. 7A

Subscriber Performance Report: Summary Page
For Evaluation on 8/14/01

| Summary | Training Set | O-Course |

SAL: 4

Select Comparison Population
- ☐ Your Fitness Club Subscribers
- ■ City-Wide Subscribers
- ☐ Regional Subscribers
- ☐ State Subscribers
- ☐ National Subscribers
- ☐ Global Subscribers
- ☐ Best-Of-The-Best Subscribers

Define Comparison Criterion
- Age [30-39 ▼]
- Gender [Female ▼]
- Program Background [6-8 Weeks in Program ▼]

[Reset Criterion]

Rankings
- Overall Attained SAL Ranking: [381] of [2,432] [16] Percentile [More Info]
- Training Set Evaluation Ranking: [204] of [2,432] [8] Percentile [More Info]
- O-Course Evaluation Ranking: [437] of [2,432] [18] Percentile [More Info]
- Weeks-In-Program Ranking: [80] of [2,432] [16] Percentile [More Info]
- Days At Present level Ranking: [619] of [2,432] [26] Percentile [More Info]

[SUBMIT]

US 8,078,478 B2

METHOD, APPARATUS, AND DATA PROCESSOR PROGRAM PRODUCT CAPABLE OF ENABLING MANAGEMENT OF ATHLETICISM DEVELOPMENT PROGRAM DATA

CROSS-REFERENCE TO RELATED APPLICATIONS

This application is a continuation of prior filed application Ser. No. 09/965,338, filed Sep. 27, 2001, which is hereby incorporated by reference.

FIELD OF THE DISCLOSURE

The disclosures herein relate generally to athletic and fitness development programs and more particularly tone or more methods, apparatuses and data processor program products capable of enabling management of athleticism development program data.

BACKGROUND OF THE INVENTION

Many people engage in fitness training routines with the intent and expectation of achieving and/or maintaining a desired level of athleticism. In some cases, such people are athletes who are no longer actively involved in a previous sport or sports. In other cases, such people are not athletes per se, but do have a competitive spirit generally associated with athleticism and have a desire to improve their level of fitness.

In each case, such people generally have a desire to both measure their progress against some defined standard and to assess the development of their fitness and athleticism among their peers in a competitive environment such that the results of their hard work are recognized. The assessment of their fitness and athletic development is a key motivating factor that positively reinforces their quest towards achieving and/or maintaining their desired level of athleticism and fitness.

Self-directed general fitness activities facilitated via a health club membership or home gym are a common approach for engaging in a fitness training routine. A facility such as a local health club or a home gym generally provides the equipment necessary to improve a person's level of fitness. However, persons motivated by factors such as recognition of their hard work, competition among peers, assessment of their progress and often loose motivation as a result of the seemingly static measures and limited feedback offered by activities and routines associated with traditional fitness development programs and facilities.

It is not that the health clubs and home gyms do not provide the equipment or tools needed to develop an athletic level of fitness. But, the individual motivation and knowledge needed to develop and/or measure balance from an athleticism perspective is often lacking. Consequently, at least a portion of health club members engage personal trainers. However, even when the training equipment is available and the knowledge from personal trainers is available, limitations associated with quantitatively assessing their athletic development and physical fitness against a set of athletic fitness standards or against peers in a self-challenging and competitive environment still exists.

Research by American Sports Data, Inc. and The International Health, Racquet & Sportsclub Association (IHRSA) verifies that traditional fitness development programs suffer from several limitations with respect to developing a desired athleticism level, quantifying a desired level of fitness and/or athleticism, and motivating one towards their desired athleticism level. One limitation is that traditional fitness development programs are not based on standardized development levels for allowing comparative assessments between program subscribers or club members. Another limitation is that there is no standard manner for determining an attained level of fitness and/or athleticism. Yet another limitation is that there is no targeted and/or quantified feedback for leveraging a fitness routine in a manner that contributes to improving a level of athleticism.

Accordingly, managing data associated with an athleticism development program in a manner that overcomes the limitations associated with techniques for managing data associated with traditional fitness and/or athleticism development program is useful.

BRIEF DESCRIPTION OF THE DRAWINGS

FIGS. 7A-7C are diagrammatic views depicting a subscriber performance report for a particular subscriber according to an embodiment of the disclosures herein.

DETAILED DESCRIPTION OF THE FIGURES

Figure 1:
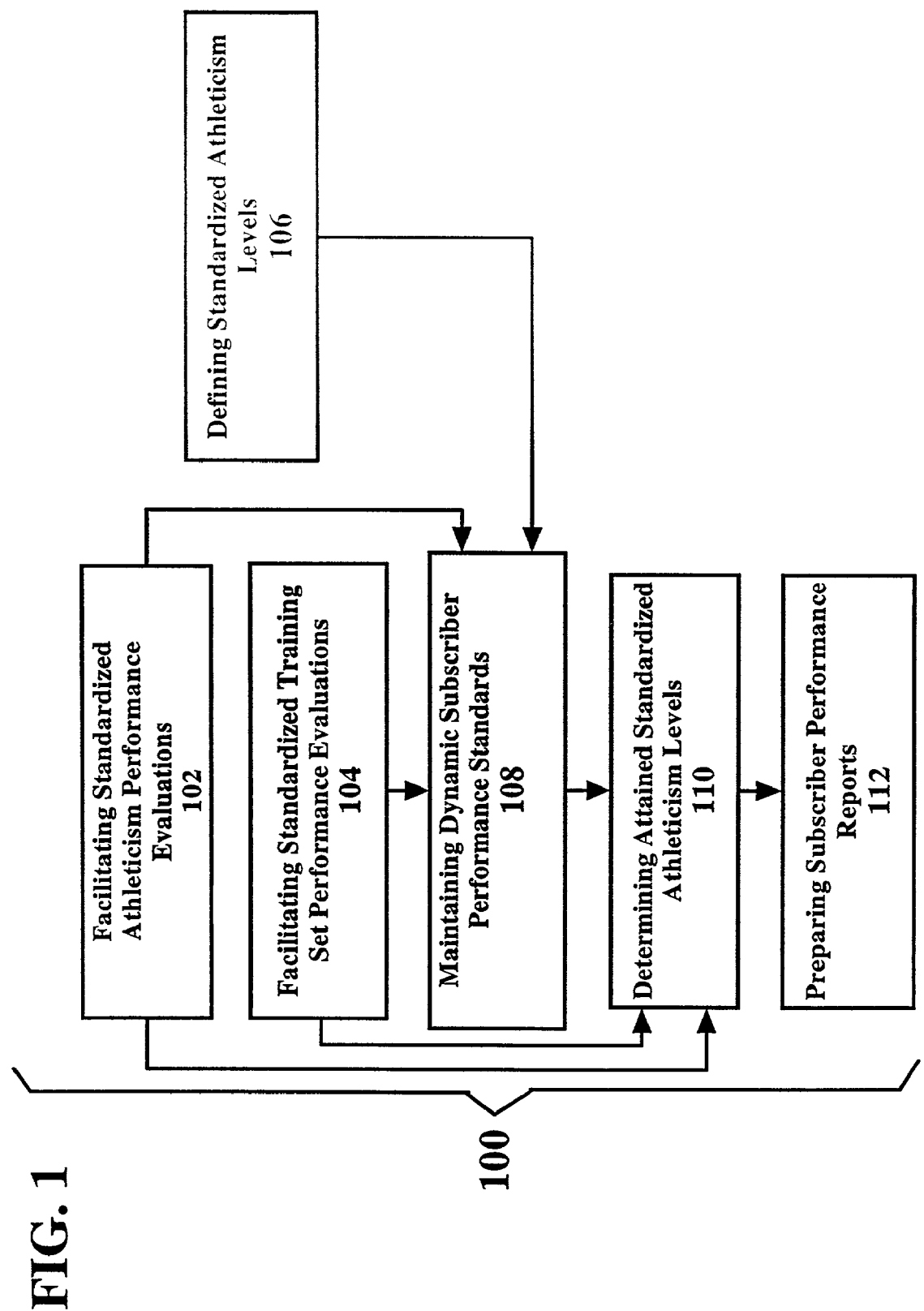
FIG. 1 is a flow chart view depicting a method capable of administering an athleticism development program according to an embodiment of the disclosures herein.

Various aspects of one or more methods, apparatuses, and data processor program products capable of enabling management of data associated with an athleticism development program are disclosed herein. These various aspects include maintaining a database including subscriber performance data for a plurality of athleticism development program subscribers and facilitating preparation of a subscriber performance report for a specified one of the plurality of athleticism development program subscribers. The subscriber performance data is capable of enabling an attained standardized athleticism level to be determined for each one of the athleticism development program subscribers.

Standardized athleticism levels are referred to hereinafter as SAL's. The implementation of SAL's is advantageous as it supports a measurable plan of progress for motivating a subscriber and trainer to meet their individual and mutual goals. In one embodiment of the athleticism development program disclosed herein, the athleticism development program is based on seven different SAL's. These seven SAL's cover a range from Novice (Level 1) to Level 7. The athleticism development program provides subscribers with a means for progressing through a goal-oriented structure, gaining balanced fitness and athleticism as they move through the various SAL's.

A number of factors contribute to administering an athleticism development program as disclosed herein being advantageous with respect to conventional fitness development programs. One factor is that balanced fitness and athletic development are capable of being achieved effectively and efficiently. Another factor is that standardized and qualitative feedback is provided in a manner that enhances individual motivation and contributes to the knowledge needed to develop balanced fitness and athletic development. Yet another factor is that athleticism development program subscribers (hereinafter referred to as subscriber) are provided with a means for testing improvements in their athletic development in a competitive environment. Furthermore, the attained standardized athleticism levels provide a means for the hard work required for achieving a particular standardized athleticism level to be recognized. Conventional fitness development programs are limited in their ability to address these and other important factors in an efficient and effective manner.

The athleticism development program disclosed herein provides a means to improve or maintain the components of physical and motor fitness through sound, progressive, balanced and goal-specific physical and athletic training. The SAL's provide subscribers with specific and quantified measures of development. Through the SAL's, subscribers are capable of measuring, monitoring and developing a true comparable level of fitness and athleticism relative to other subscribers.

Athleticism is defined herein as a balanced state of fitness in combination with an achieve level of physical performance at least partially resulting from such a state of fitness. Furthermore, it is disclosed herein that athleticism may be determined by assessing various components of athleticism. Examples of such components of athleticism are included in Table 1 below.

TABLE 1

| Component of Athleticism | Description of Component |
| --- | --- |
| Cardio Fitness | Refers to both cardio respiratory and cardio-vascular systems. Cardio respiratory refers to the efficiency with which the body delivers oxygen and nutrients needed for muscular activity and the transporting of waste products from the cells. And, cardio-vascular refers to the effectiveness of the heart and arteries to deliver blood to all parts of the body. Collectively cardio fitness provides greater respiratory endurance and oxygen processing efficiency in a body. |
| Muscular Strength | The greatest amount of force a muscle or muscle group can exert in a single effort or in multiple efforts over a short period of times. |
| Muscular Endurance | The ability of a muscle or muscle group to perform repeated movements with a sub-maximal force for extended periods of times. |
| Flexibility | The ability to move the joints (for example, elbow, knee) or any group of joints through an entire, normal range of motion. |
| Agility | The ability to employ motor functions in a fast coordinated manner demonstrating the application of speed and flexibility. |

A method 100 capable of administering an athleticism development program according to an embodiment of the disclosures herein is depicted in FIG. 1. The method 100 includes facilitating standardized athleticism performance evaluations at a block 102 and facilitating standardized training set performance evaluations at a block 104. An athleticism level assessment as disclosed and referred to herein comprises facilitating a standardized athleticism performance evaluation and facilitating a standardized fitness performance evaluation. The method 100 further includes defining standardized athleticism levels at a block 106. Maintaining dynamic subscriber performance standards is facilitated at a block 108.

Maintaining dynamic subscriber performance standards is at least partially dependent on facilitating standardized athleticism performance evaluations, facilitating standardized training set performance evaluations and defining standardized athleticism levels. Facilitating standardized athleticism performance evaluations and facilitating standardized training set performance evaluations are defined herein as being capable of generating athleticism performance data. Dynamic subscriber performance standards are defined herein as standards populated and updated with such athleticism performance data.

Determining attained SAL's for at least a portion of the subscribers is facilitated at a block 110. Preparing subscriber performance reports is facilitated at a block 112. Determining attained SAL's is at least partially dependent on facilitating standardized athleticism performance evaluations, facilitating standardized training set performance evaluations and maintaining dynamic subscriber performance standards. Preparing subscriber performance reports is at least partially dependent on determining attained SAL's. SAL's are an integral and a novel aspect of the disclosures herein. As discussed below in greater detail, SAL's provide a consistent and effective means for assessing and ranking the athletic development of subscribers.

Another novel aspect of the disclosures herein is the combined implementation of a training set performance evaluation and an obstacle course performance evaluation for determining a standardized level of athleticism. The obstacle course is hereinafter referred to as the O-course. Through the O-course performance evaluation and the training set performance evaluation, data (i.e. subscriber performance data) capable of enabling the standardized athleticism level of a subscriber to be determined is generated and captured.

The training set performance evaluation provides a means for quantitatively and individually assessing various aspects of physical fitness that are related to athleticism. It is important to assess these various aspects of physical fitness so that areas of improvement and deficiencies in physical fitness can be identified. Furthermore, by assessing these various aspects of physical fitness, the respective level of performance for these various aspects of physical fitness can be tracked and analyzed. As discussed in greater detail below, a measured parameter for each one of a plurality of training set performance evaluation components is converted to a respective score used in determining the subscriber's attained SAL. Examples of such evaluation components are present in Table 2.

TABLE 2

| Evaluation Component | Measured Parameter |
|---|---|
| Resting Heart Rate | Heat rate beats per minute |
| Body Fat | % body fat |
| Push-Ups | No. of repetitions in prescribed period of time |
| Sit-Ups | No. of repetitions in prescribed period of time |
| Step Test | Heat rate beats per minute |
| Flexibility Test | Inches of stretch according to test method |
| 1.5 mile Times Run | Time to complete test |
| T-Test | Time to complete test |
| 40-Yd. Sprint | Time to complete |

Figure 2:
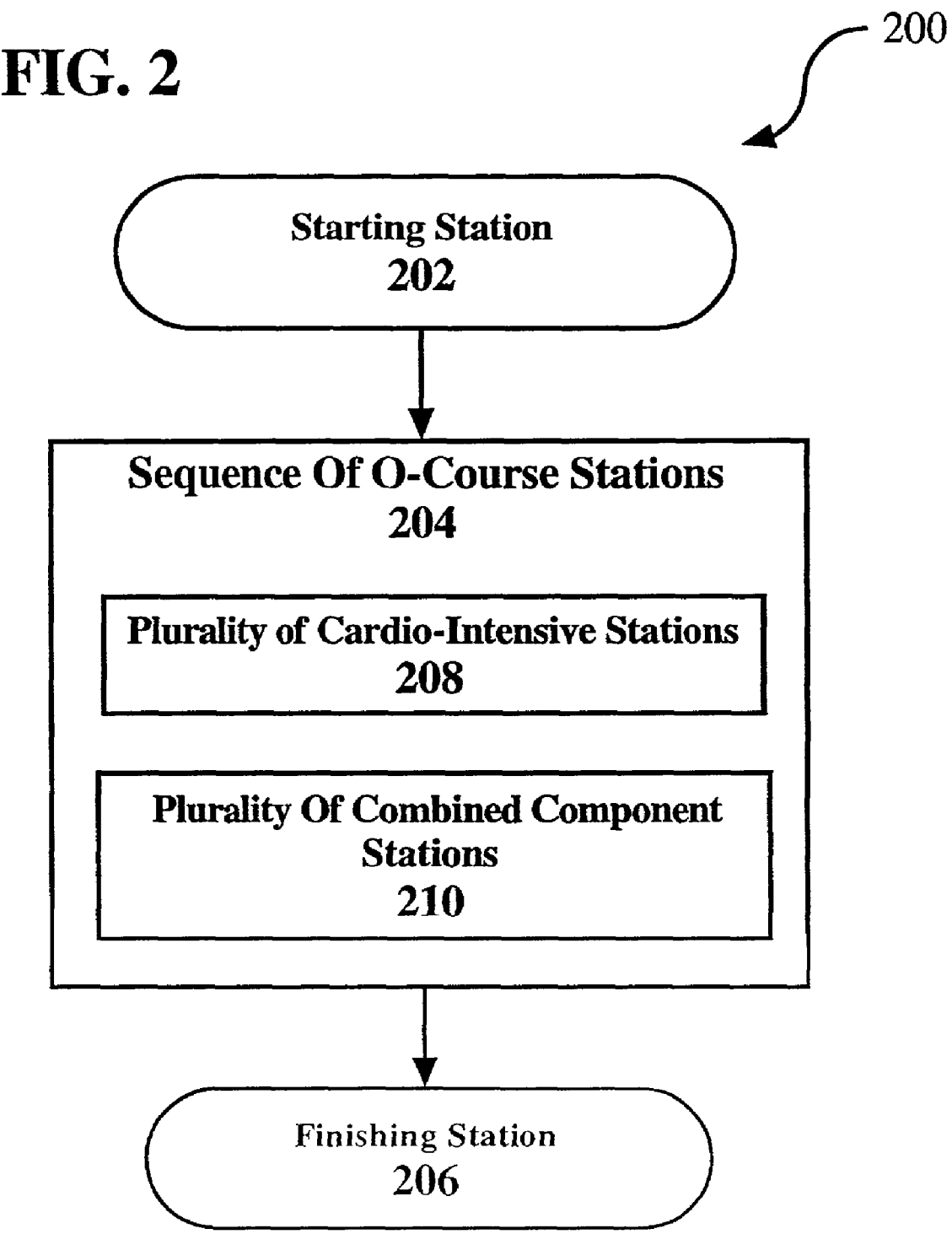
FIG. 2 is a diagrammatic view depicting an obstacle course (O-course) in accordance with an embodiment of the disclosures here.

The O-course performance evaluation provides a means for assessing the various components of athleticism in a competitive yet consistent setting. FIG. 2 depicts an O-course 200 in accordance with an embodiment of the disclosures herein. The O-course 200 is suitable for enabling the O-course performance evaluation to be facilitated. The O-course 200 includes a starting station 202, a sequence of O-course activity stations 204 and a finishing station 206. The sequence of O-course activity stations 204 includes a plurality of cardio-intensive stations 208 and a plurality of combined component stations 210. The cardio-intensive stations 208 and combined component stations 210 are examples of athleticism performance evaluation activities.

As discussed below in greater detail, the O-course provides a means of assessing the components of athleticism in a both composite and individual manner. It is important to assess the various components of athleticism in a manner to identify athletic development deficiencies. By assessing the components of athleticism in such a manner, performance relating to the composite performance and to performance in various stations of the O-course can be tracked and analyzed. Examples of stations capable of assessing certain components of athleticism and/or combinations thereof are present in Table 3.

TABLE 3

| | |
|---|---|
| Cardio Fitness | 1. Sprinting across a prescribed distance |
| | 2. Riding a stationary bicycle for a prescribed distance |
| | 3. Walking on a treadmill for a prescribed distance |
| | 4. Climbing a prescribed number of stairs on a stair stepper |
| Muscular Strength & Endurance | 1. Climbing a wall via a rope to a prescribed height |
| | 2. Climbing an inclined wall of a prescribed vertical height |
| | 3. Traversing a prescribed set of overhead bars |
| | 4. Pushing a weighted wheel barrel over a prescribed distance |
| | 5. Climbing a hanging rope to a prescribed height |
| | 6. Climbing a cargo net to a prescribed height |
| | 7. Performing a prescribed number of push-ups |
| | 8. Performing a prescribed number of pull-ups |
| | 9. Performing a rope descent over a prescribed distance |
| | 10. Performing a prescribed lunges while carrying a weight |
| Flexibility & Agility | 1. Performing a belly-crawl over a prescribed distance |
| | 2. Traversing a prescribed set of overhead bars |
| | 3. Performing a rope descent over a prescribed distance |
| | 4. Pushing a weighted wheel barrel over a prescribed distance |
| | 5. Performing a cargo net to a prescribed height |
| | 6. Traversing an elevated balance beam |
| | 7. Performing a prescribed lunges while carrying a weight |
| | 8. Jumping over a prescribed number of hurdles |

As subscribers move through the various SAL's, they are introduced at a designated SAL level to various different O-courses. A first level O-course (e.g. the "White Course") is designed to build confidence in subscribers. A second level O-course (e.g. the "Red Course") provides increased athleticism and physical fitness relative to the first level O-course. A third level O-course (e.g. the "Black Course") provides the ultimate challenge for the most fit and athletic subscribers, such as world-class athletes, top fitness performers and certified personal trainers. In each particular O-course, the number of stations, the difficulty associated with each station, and the difficulty associated with the combination of stations will dictate the level of the particular O-course. However, it should be understood that the O-courses will be designed and constructed in a standardized fashion such that there are not design and construction induced variability between O-courses at different locations.

In at least one embodiment of the O-course performance evaluation, the measure of performance is determined at least partially by an attained composite time to complete all of the station of the O-course in a pre-defined sequential manner. Also, in at least one embodiment of the O-course performance evaluation, an attained station time required to complete each of the individual stations of the O-course is captured and used to provide feedback relative to performance improvements and deficiencies associated with individual stations. To this end, each O-course may include proprietary and/or commercially available devices and systems that are capable of providing a time associated with completing an entire O-course and/or times associated with completing each individual station of an O-course.

Table 4 below depicts a subscriber performance data table for the push-ups training set performance evaluation component. The data contained in this subscriber performance data table illustrates one example of subscriber performance data as disclosed herein. Similar tables are generated for other training set performance evaluation components and the O-course performance evaluation. The age segments and level segments are administratively created and maintained with the tables being populated with actual subscriber performance data.

TABLE 4

| | AGE | | | | | | | | |
|---|---|---|---|---|---|---|---|---|---|
| Level | 17-21 Reps | 22-26 Reps | 27-31 Reps | 22-36 Reps | 37-41 Reps | 22-46 Reps | 27-51 Reps | 22-56 Reps | 27-65 Reps |
| L7 | 75+ | 76+ | 73+ | 68+ | 65+ | 61+ | 58+ | 51+ | 44+ |
| L6 | 60-74 | 61-75 | 58-68 | 53-63 | 50-61 | 47-58 | 42-52 | 36-45 | 28-37 |
| L5 | 40-59 | 41-60 | 37-53 | 33-48 | 32-46 | 26-40 | 22-37 | 16-31 | 10-25 |
| L4 | 20-39 | 21-40 | 20-33 | 18-28 | 17-27 | 14-21 | 12-20 | 10-14 | 5-8 |
| L3 | 10-19 | 9-20 | 8-18 | 5-15 | 6-15 | 5-14 | 4-13 | 3-10 | 2-6 |
| L2 | 5-9 | 5-8 | 4-7 | 4-6 | 3-6 | 3-5 | 2-4 | 2-3 | 1-2 |
| Novice | <5 | <5 | <4 | <4 | <3 | <3 | <2 | <2 | <1 |

In one embodiment of maintaining the subscriber performance data, the standards for governing performance data tables will be based initially on normalized performance charts that are in popular use to evaluate fitness and/or athletic performance in schools; the military and research based organizations. Examples of such normalized performance charts include those available from the Cooper Institute for Aerobic Research. As subscriber performance data is developed through the athleticism development program disclosed herein, the performance data tables will be populated exclusively with subscriber-specific data. In this manner, the standards and associated performance data tables will be dynamic and will reflect the real athletic, physiological and psychological changes that occur due to diet, exercising routines, life style habits, health care, scientific developments, etc.

Figure 3:
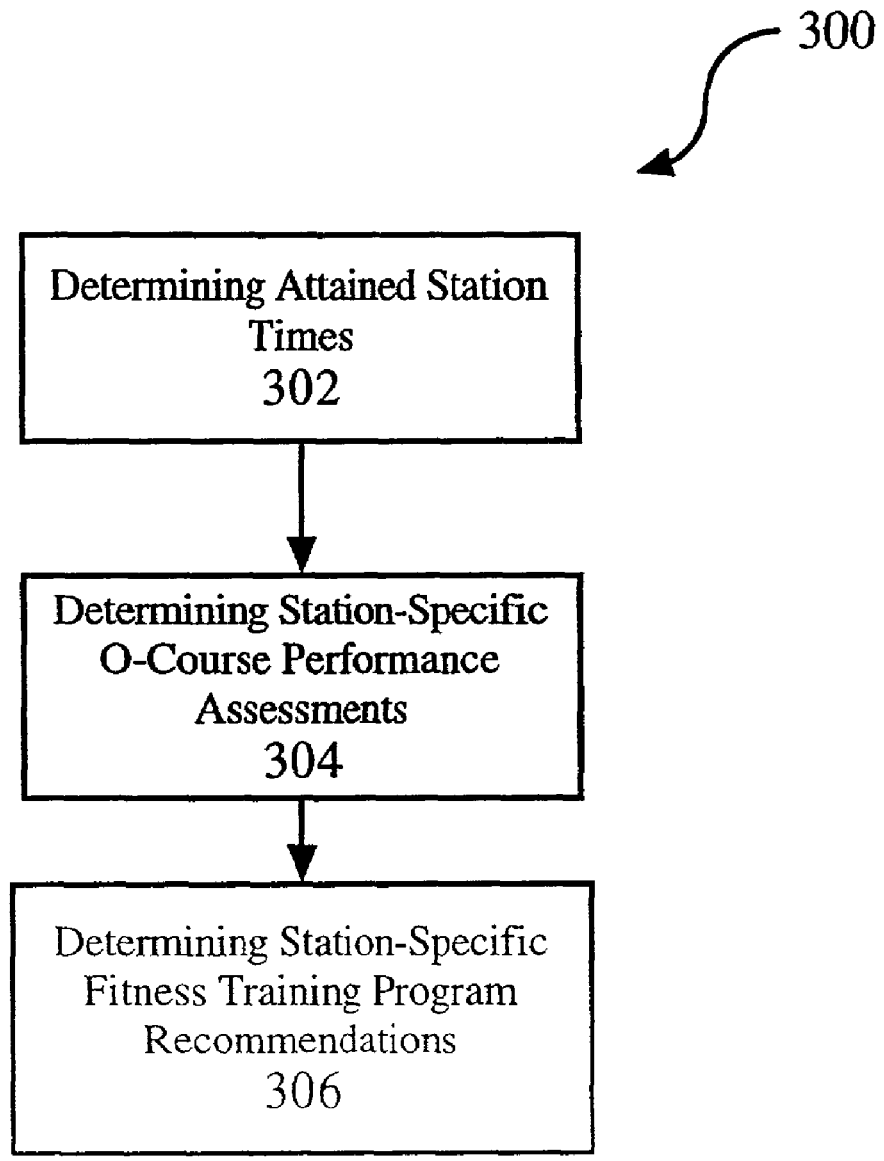
FIG. 3 is a flow chart view depicting a method capable of utilizing a station time to provide feedback relative to performance improvements and deficiencies associated with individual stations of an O-course, wherein the method is in accordance with one embodiment of the disclosures herein.

In accordance with one embodiment of the disclosures herein, FIG. 3 depicts a method 300 capable of utilizing an O-course station completion time to provide feedback relative to performance improvements and deficiencies associated with individual stations of an O-course. Determining attained station times for at least a portion of the stations of the O-course is facilitated at a block 302. After the attained station completion times are determined, an operation is facilitated for determining one or more station-specific performance assessments at a block 304. In at least one embodiment of determining one or more station-specific performance assessments, such a determination includes comparing at least a portion of the attained station completion times with baseline station times. In this manner, such an assessment is capable of determining whether a subscriber's performance at a particular station has improved or declined and, perhaps, to what degree. The baseline station completion times may be that of a particular subscriber or that of a prescribed or selected population of the athleticism development program subscribers.

After determining the one or more station-specific performance assessments, an operation is facilitated at a block 306 for determining one or more station-specific fitness training routine recommendations intended to address deficiencies in fitness and athleticism. An example of an athleticism training routine recommendation would be a recommendation to increase fitness training activities that enhance muscular strength of the lower body. More specifically, such a fitness training routine recommendation would specify that performing a prescribed number of squats or leg presses would aid in reducing the associated deficiency.

Modifying a prescribed athleticism training routine in a manner capable of at least partially overcoming the athleticism deficiency is one example of addressing deficiencies in fitness and athleticism. Adding at least one fitness training set exercise capable of at least partially overcoming the athleticism deficiency and/or adding at least one O-course stations capable of at least partially overcoming the athleticism deficiency illustrates means for modifying the prescribed athleticism training routine.

It is contemplated herein that each attained SAL may be associated with a respective one of a plurality of different O-course designs. For example a first set, a second set and a third set of the attained SAL's are associated with a first O-course design, a second O-course design and a third O-course design, respectively. In this example, the different O-course designs provide increasing level of challenge, thus providing subscribers within the associated set of attained SACS an appropriate and sufficient challenge.

Figure 4:
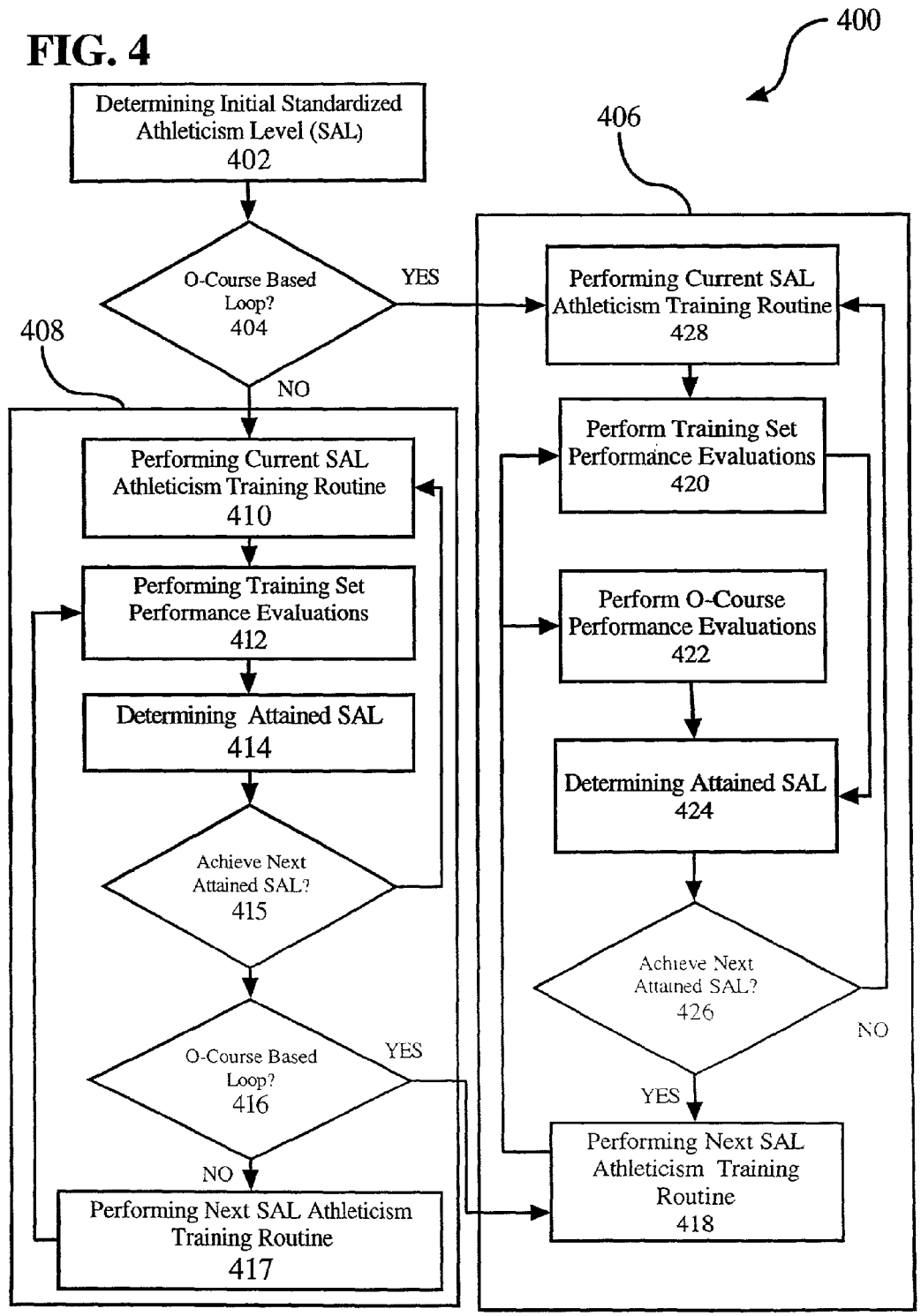
FIG. 4 is a flow chart view depicting a method capable of systematically facilitating an athleticism development program in accordance with an embodiment of the disclosures herein.

FIG. 4 depicts a method 400 capable of systematically facilitating an athleticism development program in accordance with an embodiment of the disclosures herein. At a block 402, determining an initial attained SAL is facilitated for each subscriber. Such an operation is important, as it allows each subscriber to be placed into the athleticism development program at a level consistent with his or her present level of athleticism and/or fitness.

At a block 404, it is determined whether the particular subscriber proceeds directly to an O-course based athleticism development loop 406 or to the O-course based athleticism development loop 406 via a training-set exclusive athleticism development loop 408. For example, a first set of attained SAL's may be associated with the training set exclusive athleticism development loop 408 and a second set of attained SACS may be associated with the O-course based athleticism development loop 406. The training set exclusive athleticism development loop 408 excludes an O-course performance evaluation and is intended to build the subscriber's confidence and overall level of physical fitness, thus preparing them for the performance challenge of loop 406.

In response to the subscriber's initial attained SAL resulting in placement in the training set exclusive athleticism development loop 408, the subscriber performs a current SAL athleticism training routine at a block 410. The current SAL athleticism training routine is defined herein to be an athleticism training routine consistent with the subscriber's current level of athleticism.

Accordingly, in at least one embodiment of the disclosures herein, current attained SAL athleticism training routines associated with the training set exclusive athleticism development loop 408 focus on fitness level without specific emphasis on O-course performance. It should be understood that the current attained SAL athleticism training routine may be administered and/or developed by the subscriber, a trainer or the athleticism development program administrator. Furthermore, it is contemplated and disclosed herein that the current SAL athleticism training routine may be one prepared by the athleticism program administrator, a program affiliate, a trainer or a subscriber.

After performing at least a portion of the current attained SAL athleticism training routine at the block 410, the subscriber performs a training set performance evaluation at a block 412. An attained SAL for the subscriber is determined at a block 414 after the subscriber training set performance evaluation is completed. At a block 415, it is determined whether the subscriber has advanced to the next attained SAL. It should be understood that the subscriber may have progressed to a higher attained SAL but is still within the training set exclusive athleticism development loop 408. It should also be understood that a next attained SAL for a subscriber may not be the next incremental SAL in a set of SAL's (i.e. the subscriber may have skipped one or more SAL's).

If the subscriber has not advanced to the next attained SAL, the subscriber continues with the current attained SAL athleticism training routine at the block 410. In response to the subscriber advancing to the next attained SAL, it is determined at a block 416 if the attained SAL determined at the block 414 corresponds to the subscriber having achieved an attained SAL suitable for advancing the subscriber to the O-course based athleticism development loop 406. If the attained SAL determined at the block 414 does not advance the subscriber to the O-course based athleticism development loop 406, the subscriber performs the next SAL athleticism training routine (at a block 417) corresponding to the newly attained SAL. The next SAL athleticism training routine is defined herein to be an athleticism training routine consistent with the newly attained SAL. It is contemplated herein that the next SAL athleticism development program may be the same as or different from the current SAL athleticism development program.

If the attained SAL determined at the block 414 does advance the subscriber to the O-course based athleticism development loop 406, the subscriber proceeds to the O-course based athleticism development loop 406 at a block 418. It should be understood that progression to the O-course based athleticism development loop 406 from the training set exclusive athleticism development loop 408 is based upon the subscriber moving from an attained SAL associated with the training set exclusive athleticism development loop 408 to an attained SAL associated with the O-course based athleticism development loop 406. At the block 418, the subscriber performs the next SAL athleticism training routine corresponding to the newly attained SAL. After performing at least a portion of the next SAL athleticism training routine at the block 418, the subscriber performs a training set performance evaluation at a block 420 and an O-course performance evaluation 422. An attained SAL for the subscriber is determined at a block 424 after the training set performance and the O-course performance evaluations are completed. At a block, 426, it is determined whether or not the subscriber has achieved the next attained SAL based on results from the training set performance evaluation and the O-course performance evaluation. If the subscriber has achieved the next attained SAL, the subscriber performs the next SAL athleticism training routine corresponding to the newly attained SAL at the block 418. If the subscriber has not achieved the next attained SAL, the subscriber continues with the current attained SAL athleticism training routine at the block 428. Facilitating the various athleticism training routines disclosed in reference to FIG. 4 includes one or more of the following: a plurality of training set exercises, at least one cardio intensive exercise and at least one athleticism performance assessment component.

Figure 5:
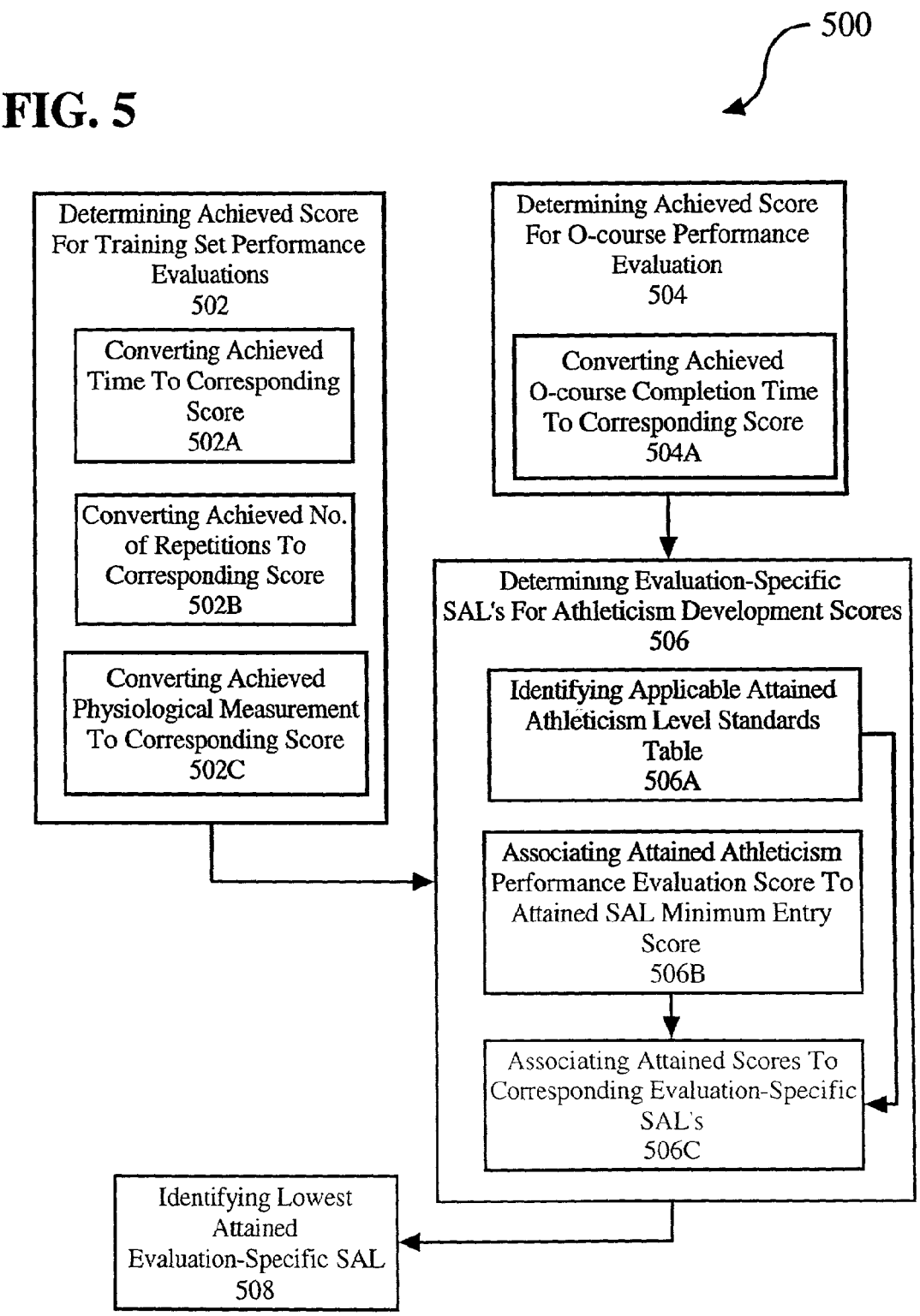
FIG. 5 is a flow chart view depicting a method capable of determining an attained SAL of a subscriber in accordance with one embodiment of the disclosures herein.

FIG. 5 depicts a method 500 capable of determining an attained SAL of a subscriber in accordance with one embodiment of the disclosures herein. The method 500 includes determining an achieved score for each one of a plurality of training set performance evaluation components (e.g. push-up test, pull-up test, 40 yd. Sprint, etc.) at a block 502 and determining an achieved score for an O-course performance evaluation at a block 504. After determining the achieved scores for the training set performance evaluation components and the O-course performance evaluation, determining evaluation-specific SAL levels for each of the training set and O-course performance evaluations is facilitated at a block 506. The training set and O-course performance evaluations are jointly referred to herein as athleticism development evaluations. By evaluation-specific, it is meant that each evaluation and/or components thereof has an associated score.

The attained SAL for the subscriber is determined by identifying the lowest of the evaluation-specific SACS at a block 508. It should be understood that the subscriber does not achieve the next attained SAL until all of the evaluation-specific SACS are equal to or greater than the next attained SAL. For example, if the subscriber achieves the next evaluation-specific SAL relative to a present attained SAL for the O-course performance evaluation and for 7 out of 8 training set performance evaluation activities, the subscriber does not advance to the next attained SAL. It is only after the subscriber achieves the next evaluation-specific SAL for all of the training set performance evaluations and the O-course performance evaluation that the subscriber advances to the next attained SAL.

Determining the achieved scores associated with the training set and O-course performance evaluations includes converting achieved quantitative results associated with a corresponding performance evaluation to a corresponding score. Determining the achieved scores for each one of the performance evaluations at the block 502 includes an operation 502A for converting one or more achieved times to a corresponding score, an operation 502B for converting one or more achieved number of repetitions to corresponding scores and an operation 502C for converting one or more achieved physiological measurement to a corresponding score. Determining the achieved score for the O-course performance evaluation at the block 504 includes an operation 504A for converting an achieved O-course completion time to a corresponding score.

At the block 506, determining evaluation-specific SAL's for the athleticism development evaluations includes an operation 506A for identifying one or more applicable SAL entry score table, an operation 506B for associating attained performance evaluation scores to attained minimum entry scores and an operation 506C for associating attained scores to corresponding evaluation-specific SACS.

Examples of achieved quantitative values include an achieved time, an achieved number of repetitions and an achieved physiological parameter. The completion times for an O-course evaluation, a 1.5 mile timed run, a 40-yard sprint and a T-test are examples of achieved times. The number of repetitions for a push-up test, a sit-up test and pull-up test are examples of achieved number of repetitions. The beats per minute of a resting heat rate measurement and percent body fat are examples of achieved physiological parameters.

Figure 6:
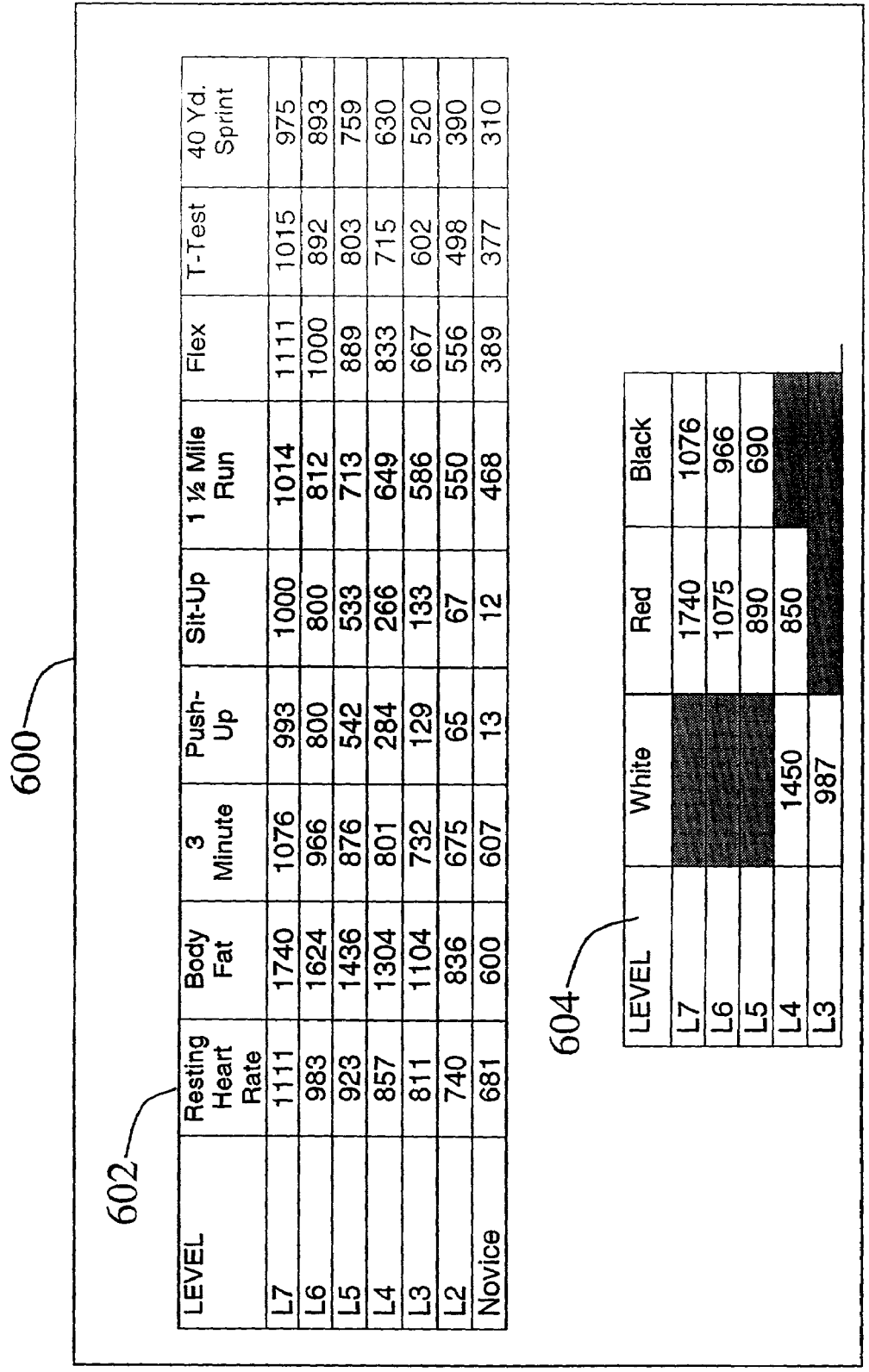
FIG. 6 is a diagrammatic view depicting a SAL minimum entry score table according to an embodiment of the disclosures herein.

FIG. 6 depicts a SAL minimum entry score table 600 according to an embodiment of the disclosures herein. The SAL minimum entry score table 600 is one of a set of SAL minimum entry score tables. The set of SAL minimum entry score tables is segmented by subscriber attributes such as, for example, gender and age.

The SAL minimum entry score table 600 includes a training set portion 602 and an O-course portion 604. The training set portion 602 includes minimum entry scores for a plurality of training set performance evaluation components. The O-course portion 604 includes minimum entry scores for a plurality of O-course deigns.

An embodiment of a scoring methodology for converting achieved quantitative results to a corresponding is disclosed herein. The scoring methodology is based on a standard score of 1,000 points for a benchmark performance. Bonus points are awarded for bettering that performance and points are deducted for failing to achieve that benchmark. Embodiments of scoring formulas are depicted below in Table 5.

TABLE 5

| Type of Achieved Quantitative Result | Scoring Formula |
| --- | --- |
| Performance based value where improvement is denoted by reducing an achieved value (e.g. O-course completion time) | 1000 × (Target Number/Member Time). (Target Number/Member Time) is a respective Scoring Factor. |
| Performance based value where improvement is denoted by increasing an achieved value (e.g. sit-up repetitions) | (1000/Target Number) × member performance. (1000/Target Performance) is a respective Scoring Factor. |
| Finite Value (e.g. body fat) | 2000 − (Target Number × Scoring Factor) Scoring Factor is determined administratively and represent a target number in the 80th and 90th percentile of subscriber results. |

EXAMPLE 1

A 45-49 year-old female subscriber has an achieved time of 21:17 (1277 sec) for a 1.5 mile run test. A target number is of 1486 seconds is applicable for a female subscriber in the age group of 45-49 participating in the 1.5 mile run test. Accordingly, this subscriber would receive a score of 1164 points (i.e. 1486/1277×1000=1163.6, rounded up to 1164).

Although not shown, minimum entry score tables for standard trainer performance levels are contemplated and disclosed herein. Trainer performance data is capable of being converted to corresponding scores such that each trainer associated with the athleticism development program may have a standardized trainer performance level associated therewith.

In at least one embodiment of a method for determining the attained standardized trainer performance level for a trainer, the method includes determining one or more attained score for a trainer performance evaluation and correlating the one or more attained score for the trainer performance evaluation to an attained standardized trainer performance level. The trainer performance evaluation is capable of assessing a plurality of trainer performance evaluation components. Examples of such trainer performance evaluation components include a number of trainer-trained subscribers, a percent retention of trainer-trained subscribers, an average improvement in an attained standardized athleticism score for each of the trainer-trained subscribers, a composite score improvement for all of the trainer-trained subscribers, a length of time at each level for each one of the trainer-trained subscribers, a time to record fitness training related data, a time to enter O-course related data, and a trainer-effectiveness parameter.

Figure 7B:
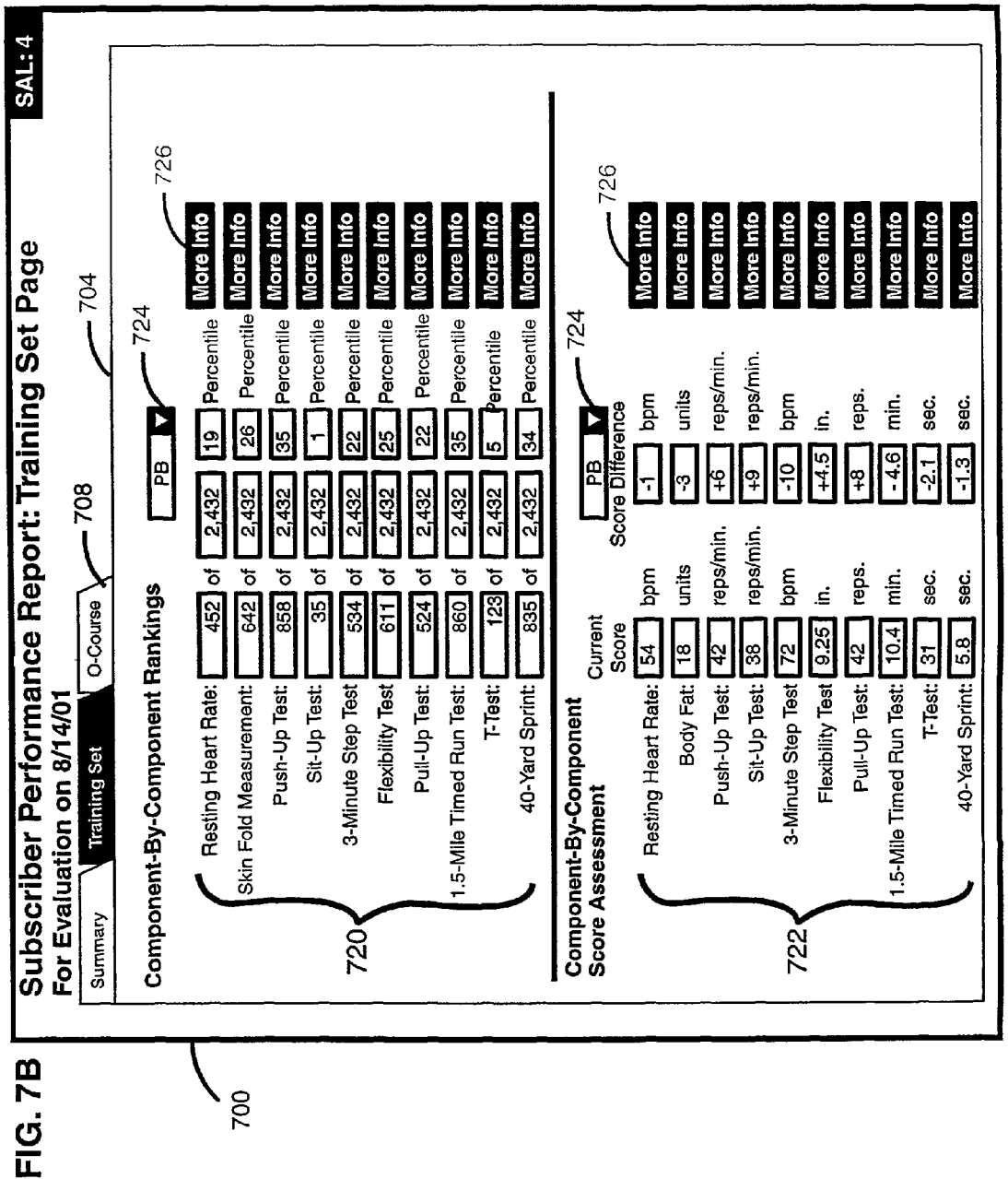
Figure 7C:
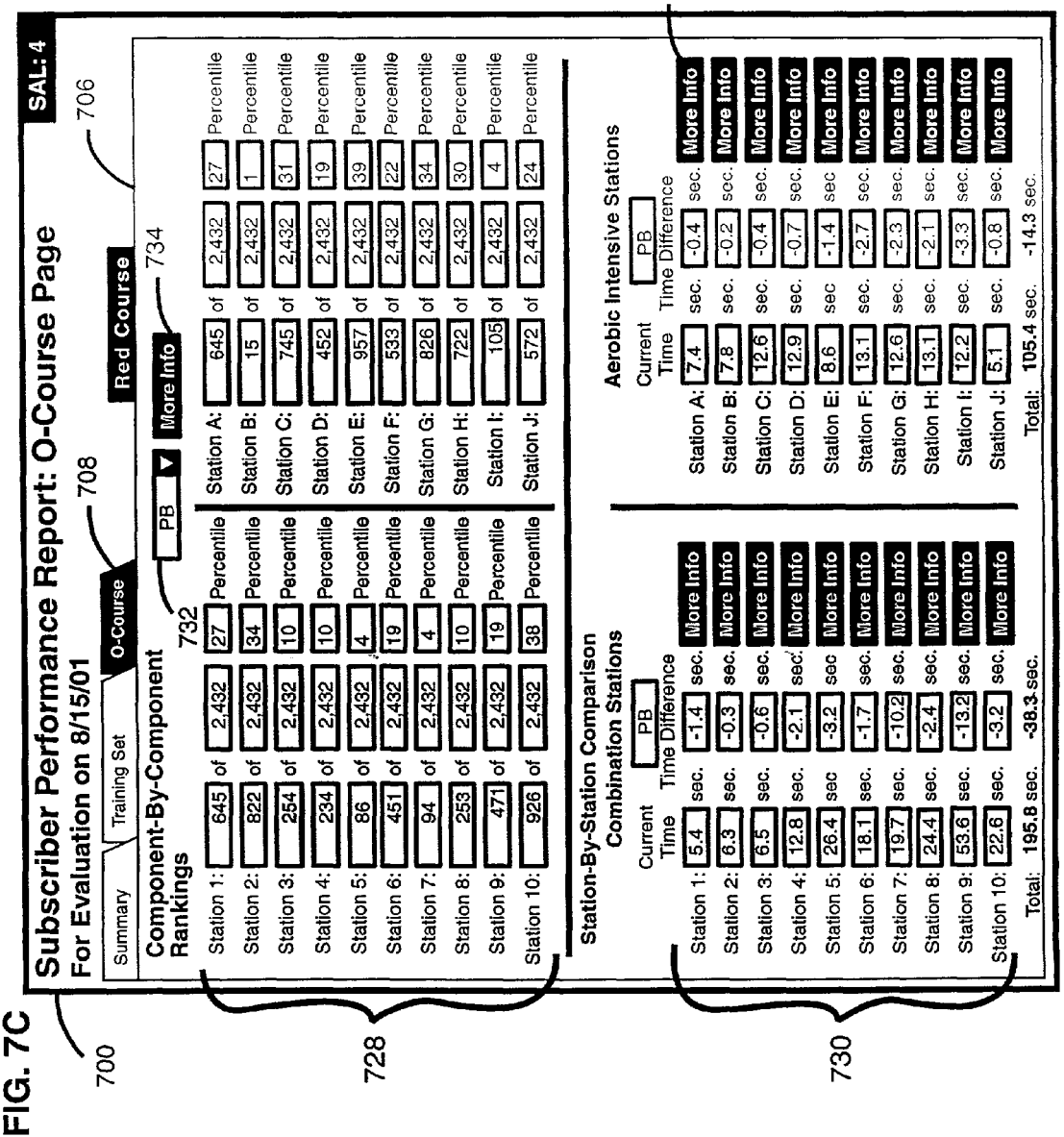

FIGS. 7A-7C depict a subscriber performance report 700 for a particular subscriber according to an embodiment of the disclosures herein. The subscriber performance report 700 is displayable on a visual display 701 of a computer system or other type of visual display device of a data processing device. The subscriber performance report 700 includes a summary page 702, a training set page 704 and an O-course. page 706. The summary page 702, the training set page 704 and the O-course page 706 are each selectable by selecting a corresponding one of a plurality of page selectors 708. A SAL indicator 710 is displayed on the visual display 701.

The summary page 702 includes a plurality of selectable comparison population fields 712, a plurality of selectable comparison criterion fields 714 and a submit button 715 for requesting preparation of the subscriber report once the desired comparison population and comparison criterion are selected. The plurality of selectable comparison population fields 712 permit a desired group of program subscribers to be selected for comparing results of the athleticism performance evaluation or evaluations of the particular subscriber. The plurality of selectable comparison criterion fields 714 permit a desired collection of subscriber attributes to be selected for further refining the group of subscribers against which the results of the athleticism performance evaluation or evaluations of the particular subscriber will be compared.

Examples of the selectable comparison population fields 712 include one or more fields that designate a subscribers at a respective fitness club, one or more fields that designate subscribers according to a respective geographical region, one or more fields that designate subscribers according to a respective benchmark level of performance. Examples of the selectable comparison criterion population fields 714 include a field that designates a range of subscriber ages, a field that designates a subscriber gender and a field that designates a subscriber program background. Examples of a field that designates a subscriber program background include a field that designates a number of weeks in the athleticism development program, a field that designates a number of weeks at a particular SAL, a field that designates a level for a test set specific athleticism level and a field that designates a level for an O-course specific athleticism level.

In response to selecting a submit button 715 after the desired comparison population and comparison criterion are selected, a plurality of ranking fields 716 are determined and displayed. Examples of the ranking fields 716 include a field that designates an overall ranking of the particular subscriber relative to attained SAL, a field that designates a ranking of the particular subscriber relative to training set performance, a field that designates a ranking of the particular subscriber relative to O-course performance, a field that designates a ranking of the particular subscriber relative to a designated time in the athleticism development program and a field that designates a ranking of the particular subscriber relative to a designated time at a particular SAL. The rankings may be designated as a particular ranking relative to the total number of subscribers in the comparison population, as a percentile of the total number of subscribers in the comparison population, or both. A "More Information" field 718 may be associated with each one of the ranking fields 716 for providing additional information for each one of the rankings.

The training set page 704, FIG. 7B, includes a plurality of training set evaluation ranking fields 720 and a plurality of component comparison field 722. The training set evaluation ranking may be designated as a ranking relative to the total number of subscribers in the comparison population, as a percentile of the total number of subscribers in the comparison population, or both. In at least one embodiment of the training set page 704, the comparison population for the training set evaluation ranking fields 720 corresponds to a selected one of the plurality of selectable comparison population fields 712 on the summary page 702.

Each one of the plurality of component comparison fields 722 compare result of a training set evaluation on a component-by-component basis for a current training set performance evaluation with respective results for a reference training set performance evaluation. A comparison selector field 724 enables a particular comparison reference parameter upon which comparisons are based to be selected. Examples of the comparison reference parameter include a personal best (PB) result for each training set component, a result for a training set performance evaluation on a designated date, etc.

A "More Information" field 726 may be associated with each one of the ranking fields 720 and with each one of the component comparison fields 722 for providing additional information for each one of the rankings and comparisons, respectively. The "More Information" field 726 may for example provide specific suggestions on exercise routines for improving the performance of the 722 components. Or, the "More Information" field 726 may or could be a motivational comment indicating that one component is very strong and suggesting that attention be paid to another to achieve the needed balance.

The O-course page 706, FIG. 7C, includes a plurality of O-course evaluation ranking fields 728 and a plurality of station comparison fields 730. The O-course evaluation ranking may be designated as a ranking relative to the total number of subscribers in the comparison population, as a percentile of the total number of subscribers in the comparison population, or both. In at least one embodiment of the O-course page 706, the comparison population for the O-course evaluation ranking fields 728 corresponds to a selected one of the plurality of selectable comparison population fields 712 on the summary page 702.

Each one-of the plurality of station comparison fields 730 compare result of an O-course evaluation on a station-by-station basis for a current O-course performance evaluation with respective results for a reference O-course performance evaluation. A comparison selector field 732 enables a particular comparison reference parameter upon which the comparison is based to be selected, Examples of the comparison reference parameter include a personal best (PB) result for each O-course station, a result for an O-course performance evaluation on a designated date, etc. A "More Information" field 734 may be associated with the ranking fields 728 and with each one of the component comparison fields 730 for providing additional information for the rankings and comparisons, respectively.

Although not shown herein, a trainer performance report and an affiliate performance report are contemplated in accordance with an embodiment of the disclosures herein. Such trainer performance and affiliate performance reports are similar in content and structure to the subscriber performance report 700 disclosed above. Examples of data contained in the trainer performance report include a number of trainer-trained subscribers, a percent retention of trainer-trained subscribers, an average improvement in an attained standardized athleticism score for each of the trainer-trained subscribers, a composite score improvement for all of the trainer-trained subscribers and a length of time at each level for each one of the trainer-trained subscribers. An example of data contained in the affiliate performance report includes an affiliate-specific ranking based on a weighting of selected trainer performance data. Examples of such trainer performance data includes number of trainer-trained subscribers, percent retention of trainer-trained subscribers, average improvement in an attained standardized athleticism score for each of the trainer-trained subscribers, composite score improvement for all of the trainer-trained subscribers and length of time at each level for each one of the trainer-trained subscribers. Such selected trainer performance data represents a weighting-based portion of the trainer performance data.

This type of data for trainer productivity enables an appropriate party at a program affiliate to better evaluate the contribution of one or more trainers and thus react more quickly to related issues that will impact the clubs revenue. Similarly some of the affiliate data is being prepared in a way (i.e. derived from the actual member activity and development results) that is unique and will allow the affiliate to manage a customer-driven business based on one or more aspects of the disclosures herein (i.e. athletic development) rather than a "feels good" approach. It is expected that this approach to measuring and utilizing trainer productivity will mesh with the goal-driven concepts of the disclosures and facilitate a longer-term membership or a subscriber or program-related relationship between the subscriber and the affiliate.

Figure 8:
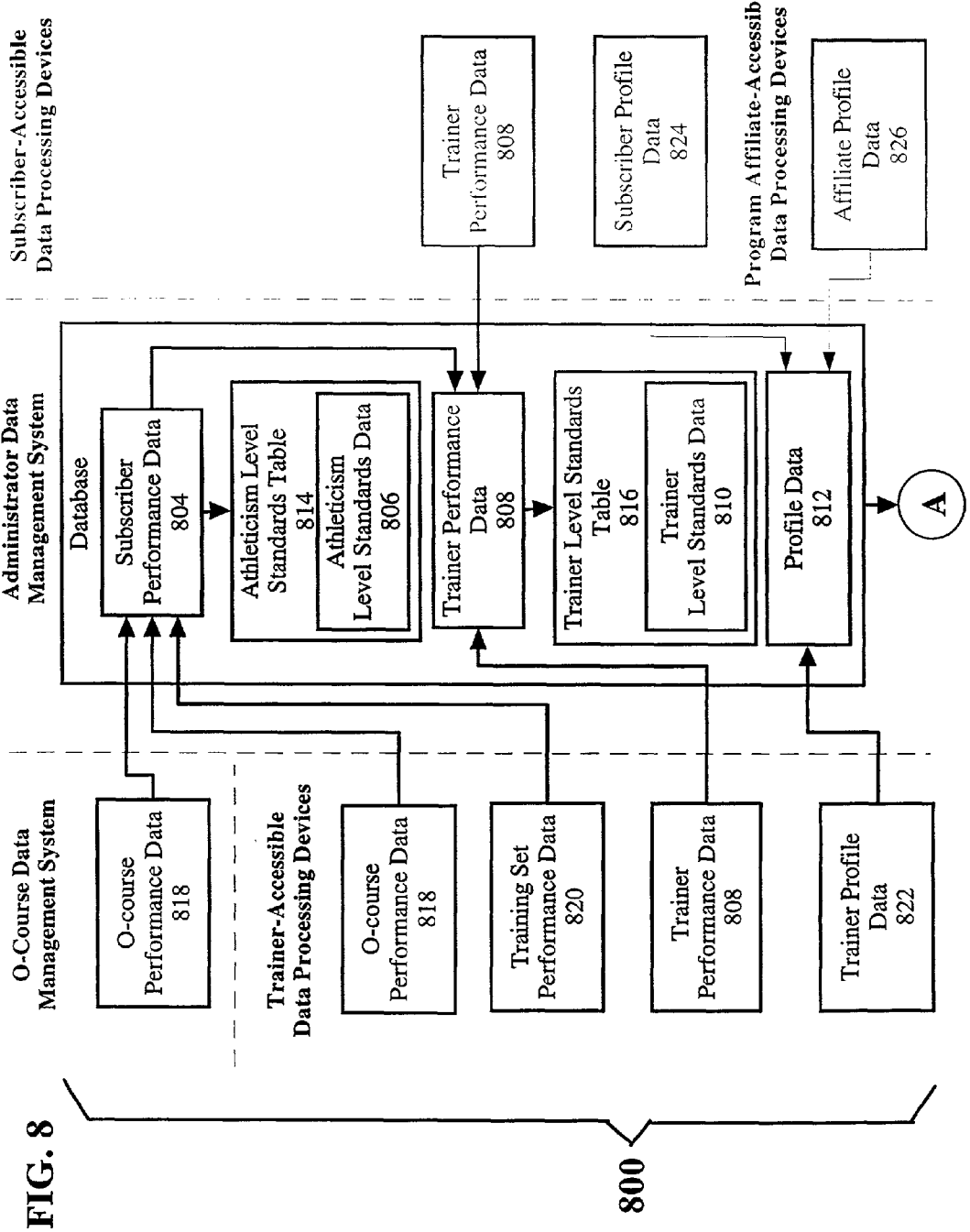
FIG. 8 is a flow chart view depicting a method for managing athleticism development program data in accordance with the disclosures herein.

FIG. 8 depicts a method 800 for managing athleticism development program data in accordance with the disclosures herein. An administrator data management system facilitates managing a database 802. The database 802 includes subscriber performance data 804, athleticism standards data 806, trainer performance data 808, trainer level standards data 810 and profile data 812. In at least one embodiment of managing the database 802, managing the database 802 includes populating an athleticism level standards table 814 with at least a portion of the subscriber performance data 804 for generating at least a portion of the athleticism level standards data 806. Similarly, in at least one embodiment of managing the database 802, managing the database 802 includes populating a trainer level standards table 816 with at least a portion of the trainer performance data 808 for generating at least a portion of the trainer level standards data 810. In this manner, each table is capable of being populated exclusively with the respective performance data. It is contemplated herein that the database 802 may comprise a plurality of relational or standalone databases.

O-course performance data 818 and training set performance data 820 are examples of the subscriber performance data 804. The database 802 is capable of receiving the O-course performance data 818 from an O-course data management system, from one or more trainer accessible data processing devices or a combination thereof. The database 802 is also capable of receiving the training set performance data 820 from one or more trainer-accessible data processing devices. Examples of the trainer-accessible data processing device includes a trainer's computer system, a computer system accessible to a trainer at an affiliate location (e.g. at a fitness club), a trainer's personal digital assistant, a trainer's wireless telephone, etc.

The database 802 is capable of receiving the trainer performance data 808 from one or more trainer-accessible data processing devices, from one or more subscriber-accessible data processing devices or a combination thereof. Examples of the subscriber-accessible data processing device includes a subscriber's computer system, a computer system accessible to a subscriber at an affiliate location (e.g. at a fitness club), a subscriber's personal digital assistant, a subscriber's wireless telephone, etc.

The database 802 is capable of receiving trainer profile data 822, subscriber profile data 824, and program affiliate profile data 826 from one or more trainer-accessible data processing devices, from one or more subscriber-accessible data processing devices and from one or more program affiliate-accessible data processing devices, respectively. The profile data 812 comprises the trainer profile data 822, the subscriber profile data 824 and the program affiliate data 826.

Figure 9:
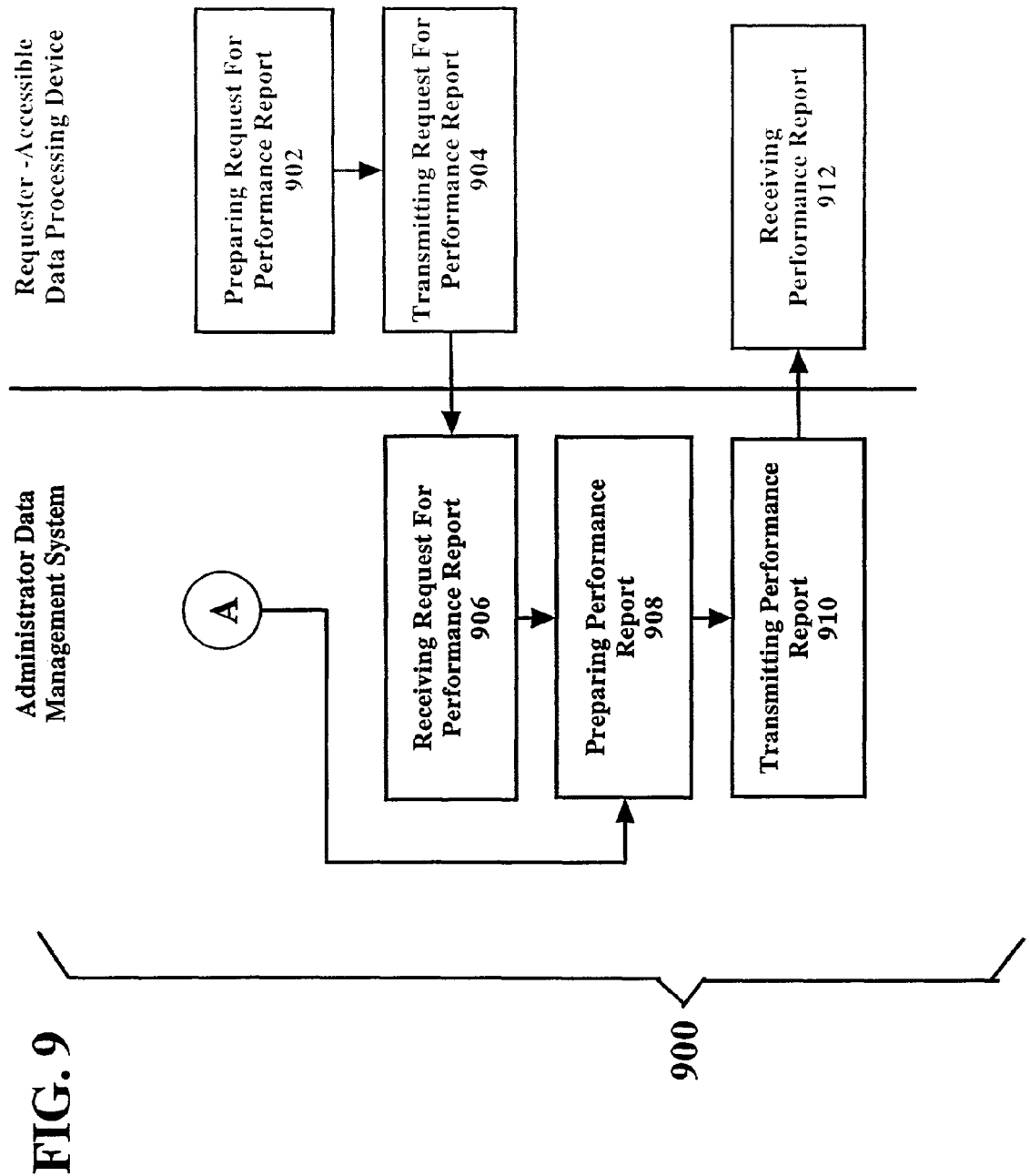
FIG. 9 is a flow chart view depicting a method capable of preparing a performance report in accordance with an embodiment of the disclosures herein.

FIG. 9 depicts a method 900 capable of preparing a performance report in accordance with an embodiment of the disclosures herein. Examples of the performance report include a subscriber performance report, a trainer performance report and an affiliate performance report. An embodiment of a subscriber performance report is disclosed in reference to FIGS. 7A-7C. An operation for preparing a request for the performance report is facilitated at a block 902 using a requester-accessible data processing device. Subscriber-accessible data processing devices, trainer accessible data processing devices and affiliate-accessible data processing devices as disclosed herein are examples of the requester-accessible data processor system.

The request for the performance report is transmitted at a block 904 from the request or accessible data processing device for being received by an administrator data management system. Performing steps such as selecting a comparison population and defining comparison criteria via web browser are examples of preparing the request for receiving the performance report. An operation is performed at a block 906 for receiving the request for the performance report.

In response to receiving the request, an operation for preparing the performance report is performed at a block 908. The operation for preparing the performance report includes receiving data from the database 802 via an entry point A. The specific type of report being generated will dictate the data received from the database 802. In response to the performance report being prepared, an operation for transmitting the performance report from the administrator data management system for being received by the requester-accessible data processing device is performed at a block 910. An operation for receiving the performance report is subsequently performed by the requester-accessible data processing device at a block 912. One embodiment of receiving the performance report includes displaying the performance report on a visual display of a computer via a web browser.

It is advantageous for various the various data and reports associated with the athleticism development program to be accessible via a computer network such as the Internet. In this manner, subscribers, trainers and affiliates can readily access authorized information and publicly available information. Accessing information via a computer network provides a means of accessing up-to-date athleticism performance evaluation data, generating reports, making reservations for scheduled classes obtaining various program documentation, etc.

Figure 10:
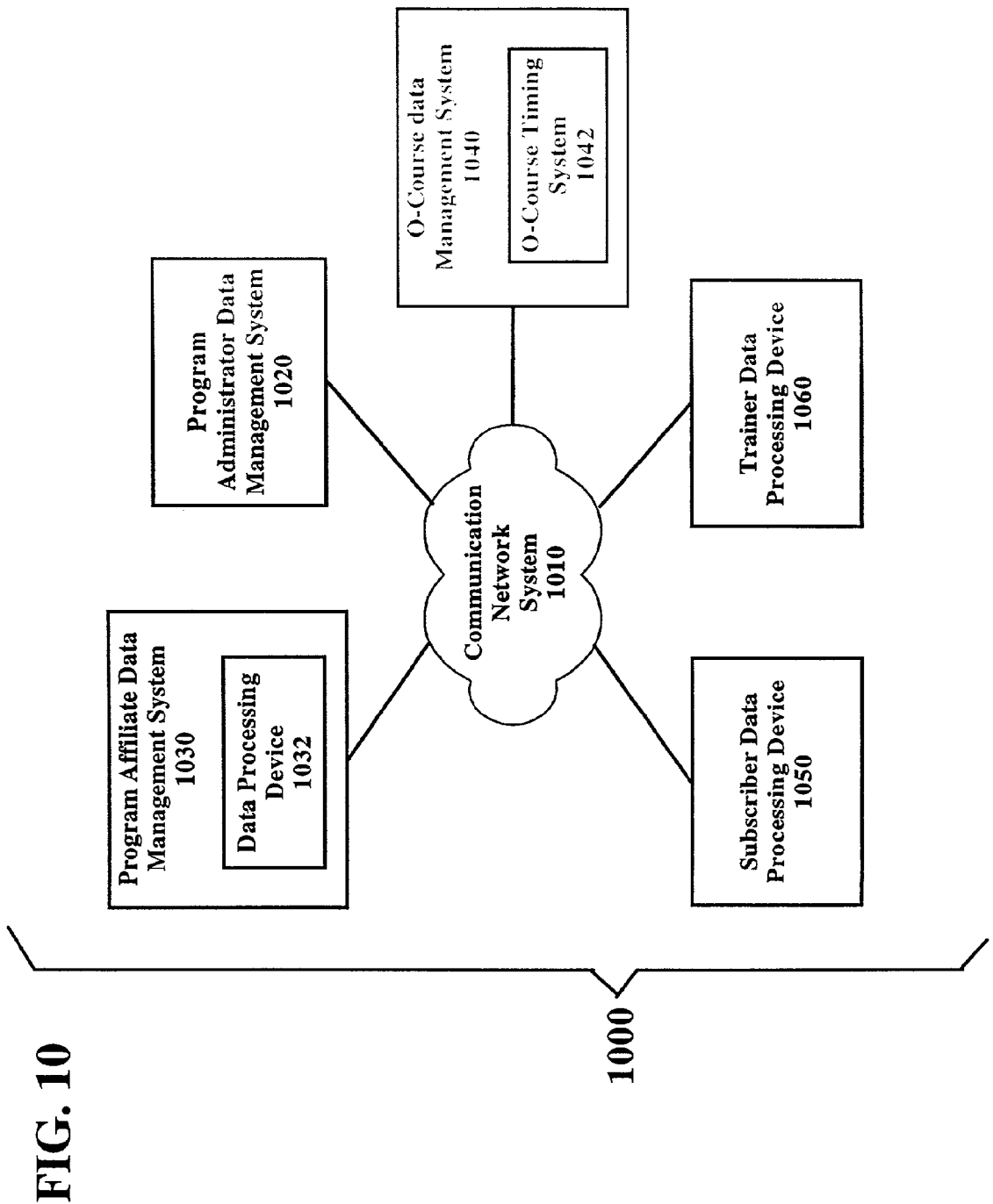
FIG. 10 is a block diagram view depicting an apparatus capable of capturing, communicating and managing athleticism development program data in accordance with an embodiment of the disclosures herein.

FIG. 10 depicts an apparatus 1000 capable of capturing, communicating and managing athleticism development program data in accordance with an embodiment of the disclosures herein. The apparatus 1000 includes a communication network system 1010, a program administrator data management system 1020, a program affiliate data management system 1030, an O-course data management system 1040, a subscriber data processing device 1050 and a trainer data processing device 1060. The program administrator data management system 1020, the program affiliate data management system 1030, the O-course data management system 1040, the subscriber data processing device 1050 and the trainer data processing device 1060 are connected to the communication network system 1010 for enabling communication there between. At least a portion of the various data management systems and data processing devices are capable of storing athleticism performance data thereon, such as on a suitable data storage device.

The program affiliate data management system 1030 includes a data processing device 1032. The data processing device 1032 depicts an example of a subscriber-accessible data processing device and a trainer-accessible data processing device. Examples of the data processing device 1032 of the program affiliate data management system 1030, the subscriber data processing device 1050 and the trainer data processing device 1060 include a computer, a digital assistant, a wired telephone and a wireless telephone.

In at least one embodiment of the communication network system 1010, the communication network system 1010 includes a plurality of different types of communication networks. Examples of the plurality of different types of networks include, but are not limited to, wireless telephone networks, public switched telephone networks, data packet networks, computer networks and the like. The Internet is a specific example of a computer network. The various networks of the communication network system 1010 are connected for enabling communication there between.

The O-course data management system 1040 includes a timing system 1042. The timing system 1042 is integrated within the O-course data management system 1040 for allowing O-course completion and station times to be captures. The timing station is capable of capturing times in an automated manner such that a high level of timing consistency and accuracy is maintained. It is contemplated herein that various commercially-available and proprietary timing systems are capable of providing the required timing functionality. Such systems may be based on optical technologies, radio frequency technologies or other suitable technologies capable of providing the required timing functionality. It is further contemplated and disclosed herein that a subscriber and/or trainer identification system (e.g. a smart card) that would contain pertinent personal and limited performance data on a chip, magnetic strip or other know type of device capable of enabling information to be accessed by a data reading system. This data would be read (e.g. downloaded) to the O-course data management system 1040 when a corresponding subscriber or trainer visits a O-course or another affiliate location so that the O-course data management system 1040 can be updated, appropriate usage fees applied, etc.

Administration of an athleticism development program as disclosed herein is capable of enabling a fitness experience more effective in terms of revenue for affiliates and trainers and in terms of results/value for subscribers. One component for enabling the fitness experience to be more effective for all parties involved is that standards are used for judging the fitness and performance of subscribers and trainers as opposed to a nebulous perception of "fitness". These standards provide for a measurable plan of progress for motivating a subscriber and trainer to meet their individual and mutual goals.

The athleticism development program disclosed herein is cost-effective for affiliates. It increases their revenue, enhances their membership retention and produces greater athletic development for their members. Another important and valuable aspect of the program is that it provides a complimentary relationship between non-associated fitness clubs, thus enhancing membership retention. The program is also fully capable of being administered on a global level such that value to subscribers, affiliates and trainers is not limited by geographical boundaries.

The O-course portion of the program serves as a competitive element to the program that can be used in a manner for evaluating and motivating subscribers on an individual, team, intra-club, inter-club and global basis. The training set portion of the program serves as a non-sport specific athletic component that is configured to meet the needs of athletes at all levels, ages and sex. In this manner, a balanced approach to physical and athletic development is provided.

Accordingly, the specification and figures herein are to be regarded in an illustrative rather than in a restrictive sense, and all such modifications and their equivalents are intended to be included within the scope of the present invention. Benefits, other advantages, and solutions to problems have been described above with regard to specific embodiments. However, the benefits, advantages, solutions to problems, and any elements that may cause any benefit, advantage, or solution to occur or become more pronounced are not to be construed as critical, required, or essential features or elements of any or all of the claims.

What is claimed is:

1. A computer-implemented method for managing athleticism development program data, comprising:

receiving subscriber-performance data for a plurality of athleticism-development-program subscribers, wherein the subscriber-performance data for each of the plurality of athleticism-development-program subscribers comprises (1) a plurality of athleticism-performance-evaluation-quantitative results ("athleticism results") and (2) a plurality of training-set-performance-evaluation-component-quantitative results ("training-set results") corresponding to a plurality of training-set-performance-evaluation components;

storing the subscriber-performance data in a database;

updating a baseline athleticism-performance-evaluation score with at least a portion of the received subscriber-performance data for the plurality of athleticism-development-program subscribers resulting in an augmented baseline score;

determining, with a processor and memory, an athleticism-performance-evaluation-achieved score based on a subscriber-specific athleticism result of the plurality of athleticism results for each of the plurality of athleticism-development-program subscribers, wherein determining the athleticism-performance-evaluation-achieved score comprises comparing each of the subscriber-specific athleticism results with the augmented baseline score;

determining, with the processor and memory, a training-set-performance-evaluation-component-achieved score based on a corresponding subscriber-specific training-set result from the plurality of training set results for each of the plurality of athleticism-development-program subscribers, wherein determining the training-set-performance-evaluation-component-achieved score comprises converting each of the subscriber-specific training-set results to a corresponding training-set-performance-evaluation-component-achieved score; and facilitating preparation of a subscriber-performance report for a specified one of the plurality of athleticism-development-program subscribers.

2. The method of claim 1, wherein the subscriber-specific athleticism result is an achieved time.

3. The method of claim 1, wherein the baseline athleticism-performance-evaluation score is an athleticism-performance-evaluation-achieved score of a selected population of the plurality of athleticism-development-program subscribers.

4. The method of claim 1, wherein facilitating preparation of the subscriber-performance report is initiated in response to receiving a request for preparing the subscriber-performance report.

5. The method of claim 1, further comprising the step of determining a ranking of a present athleticism-performance-evaluation-achieved score relative to a population of the plurality of athleticism-development-program subscribers.

6. The method of claim 1, further comprising the step of preparing a training-set-performance-evaluation-component comparison between a present training-set-performance evaluation and a reference training-set-performance evaluation.

7. The method of claim 1, further comprising the step of maintaining a plurality of athleticism-level-standards tables from which the baseline athleticism-performance-evaluation score is determined.

8. The method of claim 7, wherein maintaining the plurality of athleticism-level-standards tables comprises populating each one of the plurality of athleticism-level-standards tables with the subscriber-performance data wherein each one of the athleticism-level-standards tables is derived exclusively from a corresponding portion of the subscriber-performance data.

9. The method of claim 7, wherein maintaining each of the plurality of athleticism-level-standards tables comprises determining a minimum entry score for a plurality of standardized-athleticism levels.

10. The method of claim 9, wherein determining the minimum entry score comprises converting a reference number of repetitions to the minimum entry score, further wherein converting the reference number of repetitions to the minimum entry score comprises applying a scoring factor to the reference number of repetitions.

11. A data processor program product, comprising:
a data processor program processable by a data processor;
an apparatus from which the data processor program is accessible by the data processor; and
the data processor program being capable of enabling the data processor to facilitate:
receiving subscriber-performance data for a plurality of athleticism-development-program subscribers, wherein the subscriber-performance data for each of the plurality of athleticism-development-program subscribers comprises (1) a plurality of athleticism-performance-evaluation-quantitative results ("athleticism results") and (2) a plurality of training-set-performance-evaluation component-quantitative results ("training-set results") corresponding to a plurality of training-set-performance-evaluation components;

storing the subscriber performance data in a database;

updating a baseline athleticism-performance-evaluation score with at least a portion of the received subscriber-performance data for the plurality of athleticism-development-program subscribers resulting in an augmented baseline score;

determining an athleticism-performance-evaluation-achieved score based on a subscriber-specific athleticism result from the plurality of athleticism results for each of the plurality of athleticism-development-program subscribers, wherein determining the athleticism-performance-evaluation-achieved score comprises comparing the subscriber-specific athleticism results with the augmented baseline score;

determining a training-set-performance-evaluation-component-achieved score based on a corresponding subscriber-specific training-set result from the plurality of training-set results for each of the plurality of athleticism development program subscribers, wherein determining the training-set-performance-evaluation component-achieved score comprises converting the subscriber-specific training-set result to a corresponding training-set-performance-evaluation-component-achieved score; and preparing a subscriber-performance report for a specified one of the plurality of athleticism-development-program subscribers.

12. The data processor program product of claim 11, wherein the subscriber-specific training-set result is an achieved physiological parameter.

13. The data processor program product of claim 11, wherein the baseline-athleticism-performance-evaluation score is an athleticism-performance-evaluation-achieved score of a selected population of the plurality of athleticism-development-program subscribers.

14. The data processor program product of claim 11, wherein facilitating preparation of the subscriber-performance report is initiated in response to receiving a request for preparing the subscriber-performance report.

15. The data processor program product of claim 11, wherein the data processor program is further capable of enabling the data processor to facilitate determining a ranking of a present athleticism-performance-evaluation-achieved score relative to a population of the plurality of athleticism-development-program subscribers.

16. The data processor program product of claim 11, wherein the data processor program is further capable of enabling the data processor to facilitate preparing a training-set-performance-evaluation-component comparison between a present training-set-performance evaluation and reference training-set-performance evaluation.

17. The data processor program product of claim 11, wherein the data processor program is further capable of enabling the data processor to facilitate determining a ranking of a present training-set-performance-evaluation-achieved score relative to a population of the plurality of athleticism-development-program subscribers.

18. The data processor program product of claim 11, wherein the data processor program is further capable of enabling the data processor to facilitate maintaining a plurality of athleticism-level-standards tables in the database.

19. A system for facilitating management of athleticism development program data, the system comprising:
- a data processor;
- memory connected to the data processor; and
- a data processor program,
- wherein the data processor program is capable of enabling the data processor to facilitate:
  - receiving subscriber-performance data for a plurality of athleticism-development-program subscribers, wherein the subscriber-performance data for each of the plurality of athleticism-development-program subscribers comprises (1) a plurality of athleticism-performance-evaluation-quantitative results ("athleticism results") and (2) a plurality of training-set-performance-evaluation component-quantitative results ("training-set results") corresponding to a plurality of training-set-performance-evaluation components;
  - storing the subscriber-performance data in a database;
  - updating a baseline athleticism-performance-evaluation score with at least a portion of the received subscriber-performance data for the plurality of athleticism-development-program subscribers resulting in an augmented baseline score;
  - determining an athleticism-performance-evaluation-achieved-score based on a subscriber-specific athleticism result from the plurality of athleticism results for each of the plurality of athleticism-development-program subscribers, wherein determining the athleticism-performance-evaluation-achieved score comprises comparing the subscriber-specific athleticism result with the augmented baseline;
  - determining a training-set-performance-evaluation-component-achieved score based on a corresponding subscriber-specific training-set result from the plurality of training-set results for each of the plurality of athleticism-development-program subscribers, wherein determining the training-set-performance-evaluation-component-achieved score comprises converting the subscriber-specific training-set result to a corresponding training-set-performance-evaluation-component-achieved; and
  - facilitating preparation of a subscriber-performance report for a specified one of the plurality of athleticism-development-program subscribers.

* * * * *